United States Patent [19]

Kreighbaum et al.

[11] 4,314,943

[45] Feb. 9, 1982

[54] HETEROCYCLIC SUBSTITUTED ARYLOXY 3-INDOLYL-TERTIARY BUTYLAMINOPROPANOLS

[75] Inventors: William E. Kreighbaum; William T. Comer, both of Evansville, Ind.

[73] Assignee: Mead Johnson & Company, Evansville, Ind.

[21] Appl. No.: 11,819

[22] Filed: Feb. 13, 1979

Related U.S. Application Data

[63] Continuation-in-part of Ser. No. 815,138, Jul. 13, 1977, abandoned.

[51] Int. Cl.³ .................... A61K 31/40; C07D 209/14
[52] U.S. Cl. ........................... 260/326.13 B; 544/61; 544/143; 544/144; 544/284; 548/159; 548/186; 548/207; 548/214; 548/215; 548/341; 260/326.15; 260/326.14 R; 260/316; 424/248.57; 424/248.58; 424/251; 424/270; 424/273 R; 424/274; 544/159
[58] Field of Search ................ 260/326.15; 326.14 R, 260/326.13 B

[56] References Cited

U.S. PATENT DOCUMENTS

| | | | |
|---|---|---|---|
| 3,471,515 | 10/1969 | Troxler et al. | 260/326.15 |
| 3,910,924 | 10/1975 | Tamura et al. | 424/258 |
| 3,954,776 | 5/1976 | Muro et al. | 260/326.5 D |
| 3,982,012 | 9/1976 | Fauland et al. | 424/273 |
| 3,984,436 | 10/1976 | Jaeggi et al. | 260/326.5 L |
| 4,053,601 | 10/1977 | Coates et al. | 424/250 |
| 4,056,626 | 11/1977 | Ito et al. | 424/285 |
| 4,067,873 | 1/1978 | Troxler et al. | 424/258 |
| 4,072,683 | 2/1978 | Nakagawa et al. | 424/258 |
| 4,073,909 | 1/1978 | Troxler et al. | 424/258 |
| 4,076,829 | 2/1978 | Kampe et al. | 424/274 |
| 4,080,463 | 3/1978 | Troxler et al. | 260/326.15 |
| 4,081,447 | 3/1978 | Prasad et al. | 424/288 |
| 4,085,114 | 4/1978 | Adachi et al. | 424/272 |
| 4,120,963 | 10/1978 | Kampe et al. | 424/256 |
| 4,139,623 | 2/1979 | Jaeggi et al. | 424/251 |
| 4,143,149 | 3/1979 | Wiedemann et al. | 424/273 P |
| 4,144,344 | 3/1979 | Eichenberger et al. | 424/267 |
| 4,146,630 | 3/1979 | Kampe et al. | 424/267 |
| 4,186,131 | 1/1980 | Kreighbaum et al. | 548/251 |
| 4,234,595 | 11/1980 | Kreighbaum et al. | 260/326.15 B |

OTHER PUBLICATIONS

Läubie et al., "Arch Int. Pharmacodyn", vol. 201, 1973, pp. 323–333.
Hassle, "Derwent Publications", No. 26952A/15.
"Derwent Publications", No. 80147A/45.
Bartsch et al., "Pharm. Chem. Research Labs.", 1977.
Obase et al., "Chem. Pharm. Bull.", vol. 26, No. 5, 1978, pp. 1443–1452.

*Primary Examiner*—Donald G. Daus
*Assistant Examiner*—James H. Turnipseed
*Attorney, Agent, or Firm*—Robert H. Uloth; Robert E. Carnahan

[57] ABSTRACT

1-Aryloxy-3-[(3-indolyl)-tert.-butyl]amino-2-propanols having a heterocyclic aryl-attached substituent or aryl-fused heterocyclic ring are antihypertensive agents having vasodilator and adrenergic β-receptor blocking action.

5 Claims, No Drawings

HETEROCYCLIC SUBSTITUTED ARYLOXY 3-INDOLYL-TERTIARY BUTYLAMINOPROPANOLS

REFERENCE TO RELATED APPLICATION

This application is a continuation-in-part of co-pending application Ser. No. 815,138 filed July 13, 1977 now abandoned.

FIELD OF THE INVENTION

The present invention is concerned with heterocyclic carbon compounds of the indole series having an amino substituent, and with drug, bio-affecting and body-treating processes employing these compounds. The amino substituent contains an additional heterocyclic group such as pyrrole or pyrrolidine attached or fused to a phenyl ring which are classified in various subclasses.

DESCRIPTION OF THE PRIOR ART

I. A substantial body of prior art has developed during the last ten years involving compounds of the 3-aryloxy-2-hydroxypropylamine series which have β-adrenergic receptor blocking activity and are useful in the treatment of cardiovascular diseases. These structures are typified by the substance 1-isopropylamino-3-(1-naphthoxy)-2-propanol which is currently in medical use under the non-proprietary name propranolol. Propranolol and a related group of naphthoxypropanolamines are the subject of U.S. Pat. No. 3,337,628 patented Aug. 22, 1967. A large number of patents have been granted since that time on carbocyclic ethers in which other aromatic rings replace the naphthoxy group of propranolol. Many of these compounds are in the phenoxy series and others are phenoxy compounds with a fused heterocyclic ring.

II. The following patents and publications describe 3-indolylalkylamino compounds.

Robinson, U.S. Pat. No. 2,908,691 patented Oct. 13, 1959 describes a group of 3-indolylalkylamines having an aralkyl substituent attached to the amino nitrogen atoms. These substances have utility as hypnotic, anti-secretory, and anti-emetic agents. The product of Example 7 thereof has been referred to as SC10049 having bronchodilator and hyperglycemic action (Van Arman, J. Pharmacol. and Exptl. Therap. 133, 90–97 (1961)).

Wasson, et. al., U.S. Pat. No. 3,946,009 patented Mar. 23, 1976 disclose a group of pyrazinyloxypropanolamines among which the 3-indolyl-tert.-butyl group is mentioned as an amino substituent. Refer to column 22, line 15. These substances have adrenergic β-receptor blocking properties.

Jackman, G. B., et al., J. Pharm. Pharmacol., 1965 17, 742-746 entitled "Some Tryptamine Derivatives; 1-Aryloxy-3-[(2-indol-3'-ylethyl)amino]propan-2-ols". 3-Indolylethylaminopropanols were conceived of as central nervous system agents of the tranquilizer type. The only compound found to possess any activity had the structural formula shown below. It reflected only a fraction of the CNS activity of chlorpromazine hydrochloride in laboratory tests, and was considered not worthy of detailed biological study.

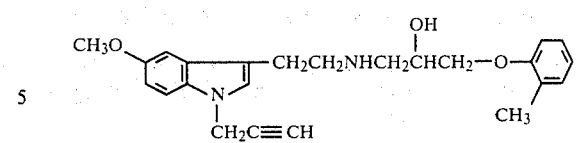

III. The following patent discloses various heterocyclic alkylaminopropanols but no indole compounds are disclosed.

Augstein, et al. U.S. Pat. No. 3,852,291 patented Dec. 3, 1974. Pyrimidinyl alkylamino and imidazolinylalkylamino propanols are described which have adrenergic β-receptor blocking action.

IV. The following patents describe aryloxypropanolamino compounds in which the aryloxy group bears a heterocyclic substituent. Indolylalkylamino substituents are absent.

McLoughlin, et al., U.S. Pat. No. 3,328,417 patented June 27, 1967 disclose 2-pyridyl, 2-indolyl, 2-benzoxazolyl, 2-benzthiazolyl, 2-quinolyl, 2-quinoxolyl, 4-thiazolyl, and 3-thienyl as phenoxy substituents.

A. B. Hassle, Belg. Pat. No. 859,474 published Apr. 7, 1978 (Derwent Publications, Ltd., Accession No. 26952A/15). The phenoxy substituents disclosed are morpholino, pyrrolidino, or pyrrolyl.

Muchowski, et al., U.S. Pat. No. 3,940,407 patented Feb. 24, 1976 disclose 4- or 5-(1,2,3)-thiadiazolyl as phenoxy substituent.

Muro, et al., U.S. Pat. No. 3,954,776 patented May 4, 1976 disclose 2-thienylmethyl, 2-pyridylmethyl, 2-pyridyl, 2-furfuryloxy, 2-thienylmethoxy, and 2-pyridyloxy as phenoxy substituents.

Jaeggi, et al., U.S. Pat. No. 3,984,436 patented Oct. 5, 1976 disclose a series of phenoxypropanolamines in which the phenoxy substituent is further substituted by the 1-pyrrolyl group. These compounds are blockers of adrenergic β-receptors.

Coates, et al., U.S. Pat. No. 4,053,601 patented Oct. 11, 1977 disclose 3-oxo-4-pyridizinyl as phenoxy substituent.

V. The following patents describe aryloxypropanolamino compounds in which the aryl group is phenyl having a fused heterocyclic ring.

Troxler, Canadian Pat. No. 834,751 issued Feb. 17, 1970; Troxler, et al. U.S. Pat No. 3,471,515 patented Oct. 7, 1969; Troxler, U.S. Pat. No. 4,080,463 patented Mar. 21, 1978; and Kampe, et al., U.S. Pat. No. 4,076,829 patented Feb. 28, 1978 disclose compounds in which the aryl group is 4-indolyl.

Tamura, et al., U.S. Pat. No. 3,910,924 patented Oct. 7, 1975; Nakagowa, et al., U.S. Pat. No. 4,072,683 patented Feb. 7, 1978; and Prasad, et al., U.S. Pat. No. 4,081,447 patented Mar. 28, 1978 disclose compounds in which the aryl group is 2-oxo-1,2,3,4-tetrahydro-5-quinolinyl.

Ito, et al., U.S. Pat. No. 4,056,626 patented Nov. 1, 1977 disclose compounds in which the aryl group is 4-, 5-, 6- or 7-benzo[b]-furanyl.

Adachi, et al., U.S. Pat. No. 4,085,114 patented Apr. 18, 1978 disclose compounds in which the aryl group is 4-, 5-, 6- or 7-benzo[d]isoxazolyl.

Kampe and Senn, et al., U.S. Pat. No. 4,120,963 patented Oct. 17, 1978, disclose compounds in which the aryl group is 1-oxo-2-methyl-1,2-dihydro-5,6,7 or 8-β-carbolinyl.

Seeman, U.S. Pat. No. 3,965,095 patented June 22, 1976 discloses compounds in which the aryl group is oxindole.

Fauland, et al., U.S. Pat. No. 3,982,012 patented Sept. 21, 1976 disclose compounds in which the aryl group is 4-benzo[d]imidazolyl.

SUMMARY OF THE INVENTION

The present invention includes the compounds of Formula II and the acid addition salts of these substances Formula II

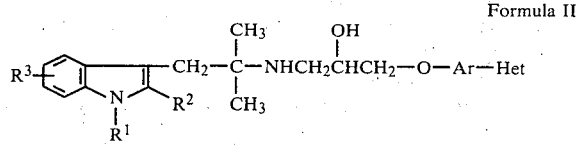

In the foregoing structural formula the symbols $R^1$, $R^2$, $R^3$, Ar and Het having the following meanings.

$R^1$ or $R^2$ is hydrogen and the other is hydrogen or alkyl having 1 to 4 carbon atoms, $R^3$ is H, halogen (including chlorine, bromine, fluorine, and iodine), alkyl having 1 to 4 carbon atoms, or alkoxy having 1 to 4 carbon atoms and is located in the 4-, 5-, 6-, or 7- positions of the indole ring, Ar is phenyl, Het is an Ar-attached heterocyclic substituent selected from the group consisting of
1-pyrrolyl,
2-oxo-1-pyrrolidinyl having a substituent in the 4-position selected from aminocarbonyl, alkylaminocarbonyl, dialkylaminocarbonyl, and alkoxycarbonyl, wherein said alkyl and alkoxy groups have 1 to 4 carbon atoms,
4-morpholinyl,
4-thiamorpholinyl,
3-oxo-1-pyrazolidinyl,
2-imidazolyl,
furfuryloxy,
2-thiazolyl, or Ar-Het as a unit is selected from the group consisting of
4-indolyl,
8-(2,3-dihydro)benzo[b]thiapyranyl,
4-oxindolyl,
6-benzo[d]thiazoyl,
4-dibenzofuranyl,
4-carbazolyl,
4-alkyl-7-alkoxy-6-quinazolinyl, and
4-alkyl-6-alkoxy-7-quinazolinyl
wherein said alkyl and alkoxy groups have 1 to 4 carbon atoms.

The compounds of the present invention are unique as anti-hypertensive agents in that they combine adrenergic β-receptor blocking and vasodilator activity. They also have utility as anti-anginal agents, anti-stress agents, antiarrhythmic agents, anti-thrombogenic agents and in the treatment of conditions where it is desirable to reduce the oxygen demand of the heart such as post-myocardial infarct management. Preferred members have a particularly desirable combination of the foregoing actions, and ancillary pharmacological effects, or a lack thereof, which particularly suits them for specific indications from among those listed. The utility of the compounds of Formula II can be demonstrated in various animal models including antagonism of isoproterenol in the conscious rat treated orally (adrenergic β-receptor action), the spontaneous hypertensive rat (antihypertensive action), the dog hind limb preparation (vasodilator action), angiotensin-maintained ganglion blocked rat model (vasodilator action), ouabain-induced ventricular tachycardia in the dog (antiarrhythmic action), in the coronary artery occluded dog (antiarrhythmic action), in vitro by measuring platelet aggregation in platelet-rich plasma photometrically following challenge with a thrombogenic agent such as adenosine diphosphate or collagen (antithrombogenic action), and in various other animal and laboratory models.

DETAILED DESCRIPTION OF THE INVENTION

The invention includes compounds having the foregoing structural formula and the acid addition salts thereof. For medical use, the pharmaceutically acceptable acid addition salts are preferred. The pharmaceutically acceptable acid addition salts are those salts in which the anion does not contribute significantly to the toxicity or pharmacological activity of the salt, and as such, they are the pharmacological equivalents of the bases having the foregoing structural formulas. In some instances, the salts have physical properties which make them more desirable for pharmaceutical formulation purposes such as solubility, lack of hygroscopicity, compressibility with respect to tablet formation and compatibility with other ingredients with which the substances may be used for pharmaceutical purposes. Acid addition salts which do not meet the foregoing criteria for pharmaceutical acceptability, for instance as to toxicity, are sometimes useful as intermediates for isolation and purification of the present substances or for other chemical synthetic purposes such as separation of optical isomers. Such salts are also part of the invention.

The acid addition salts are made by reaction of a base of the foregoing structural formula with the acid preferably by contact in solution. They may also be made by metathesis or treatment with an anion exchange resin whereby the anion of one salt of the substance is replaced by another anion under conditions which allows for separation of the undesired species such as by precipitation from solution or extraction into a solvent or elution from or retention on an anion exchange resin. Pharmaceutically acceptable acids for the purposes of salt formation include hydrochloric, hydrobromic, hydroiodic, citric, acetic, benzoic, phosphoric, nitric, mucic, isethionic, methanesulfonic, p-toluenesulfonic, glucosaccharic, palmitic, heptanoic, oxalic, cyclamic, succinic, malic, fumaric, mandelic, malonic, and others.

The compounds of the present invention shown by the foregoing structural formula contain an asymmetric carbon atom in the propanolamine side chain and occur as optically active isomers as well as racemic mixtures thereof. The present invention is intended to include each of the optically active and racemic forms. Some of the substances of the present invention contain an asymmetric carbon atom in the Het substituent, and diastereoisomeric pairs of racemates exist. These forms are also included.

Resolution of racemic mixtures to provide the optically active isomers of the foregoing compounds is carried out, for example, by forming a salt with an optically active acid many of which are known to those skilled in the art such as optically active tartaric, mandelic, cholic, O,O,-di-p-toluoyl tartaric, and O,O-dibenzoyl tartaric acids, or other acids conventionally employed for this purpose. The claims, therefore, will be understood to embrace the products in the form of the several racemic mixtures as well as in the form of the optically active isomers where appropriate.

The therapeutic processes of this invention comprise systemic administration of an effective, non-toxic amount of a compound of Formula II or a pharmaceutically acceptable acid addition salt thereof to a mammal having a condition in which therapeutic benefit is derived from a reduction in activation of the adrenergic $\beta$-receptors, or to a mammal having a condition in which therapeutic benefit is derived from vasodilation, or to a mammal having hypertension. An effective amount is construed to mean a dose which exerts an adrenergic $\beta$-receptor blocking action, a vasodilator effect, or antihypertensive action in the affected animal without undue toxic side effects. By systemic administration, it is intended to include both oral and parenteral routes. Examples of parenteral administration are intravenous injection or infusion, and intraperitoneal, intramuscular or subcutaneous injection. Rectal administration by ointment or suppository may be employed. Dosage will vary according to the route of administration with from about 0.1 mcg to 100 mg/kg body weight of a compound of Formula II or a pharmaceutically acceptable acid addition salt thereof generally providing the desired therapeutic effect. Acute toxicities measured in the mouse treated orally are within the range of about $ALD_{50}$ 125 mg/kg to >2000 mg/kg of body weight, with non-lethal signs of drug effect such as central nervous system stimulation or depression, mydriasis, or lacrimation appearing at from ½ to 1/10 that dose.

For the preparation of pharmaceutical compositions containing the compounds of Formula II in the form of dosage units for oral administration, the compound is mixed with a solid, pulverulent carrier such as lactose, sucrose, sorbitol, mannitol, potato starch, corn starch, amylopectin, cellulose derivatives, or gelatin, as well as with glidents such as magnesium stearate, calcium stearate, polyethylene glycol waxes or the like and pressed into tablets. The tablets may be used uncoated or coated by known techniques to delay disintegration and absorption in the gastrointestinal tract and thereby provide a sustained action over a longer period. When coated tablets are wanted, the above prepared core may be coated with a concentrated solution of sugar, which solution may contain e.g. gum arabic, gelatin, talc, titanium dioxide or the like. Furthermore, the tablets may be coated with a lacquer dissolved in an easily volatile organic solvent or mixture of solvents and if desired, dye may be added to this coating.

In the preparation of soft gelatin capsules consisting of gelatin and e.g. glycerine and the like, the active ingredient is mixed with a vegetable oil and encapsulated in conventional manner. Hard gelatin capsules may contain granules of the active ingredient in combination with a solid, pulverulent carrier such as lactose, saccharose, sorbitol, mannitol, starch (such as e.g. potato starch, corn starch, or amylopectin), cellulose derivatives or gelatin.

Dose units for rectal administration may be prepared in the form of suppositories containing the compound in a mixture with a neutral fat base, or in the form of a gelatin-rectal capsule with a mixture of vegetable oil or paraffin oil.

Liquid preparations suitable for oral administration are suspensions, syrups and elixirs containing from about 0.2% by weight to about 20% by weight of the active ingredient.

A suitable injectible composition comprises an aqueous solution of a water soluble pharmaceutically acceptable acid addition salt adjusted to physiologically acceptable pH.

The compounds of Formula II are prepared by application of known processes to the appropriate starting materials. Representative known methods for the preparation of aryloxypropanolamine compounds are disclosed in the foregoing patents and publications cited above under Description of the Prior Art of which the Troxler Canadian Pat. No. 834,751 and the Jaeggi, et al., U.S. Pat. No. 3,984,436 are illustrative. More specifically, the present invention provides a process for the preparation of the compounds of Formula II according to the following reaction scheme.

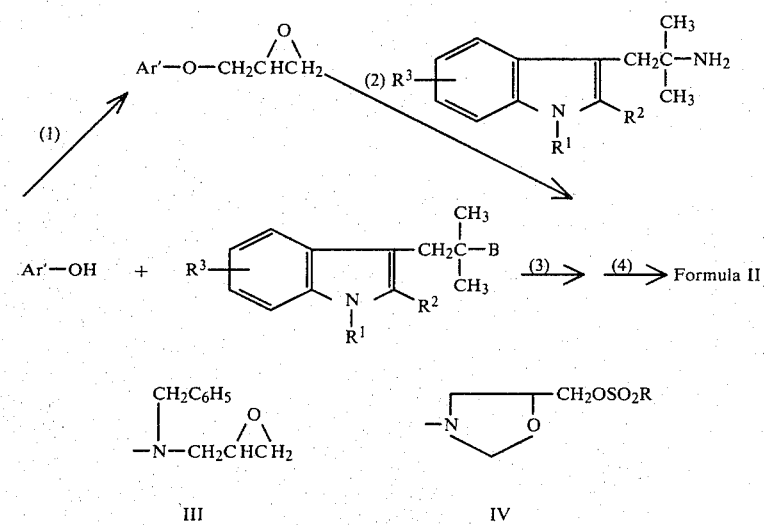

In the foregoing reaction scheme, $R^1$, $R^2$, and $R^3$ have the same meaning as before, the symbol Ar' represents the group Ar-Het as defined for Formula II with respect to Ar and Het individually and collectively, and the symbol B is defined by Formulas III and IV in which R is a lower alkyl group of 4 or fewer carbon atoms. The preferred method is according to reactions (1) and (2) in which step (1) involves reacting the appropriately substituted phenolic compound Ar'-OH with epichlorohydrin or epibromohydrin in the presence of a catalytic quantity of an amine followed by treating with aqueous alkali metal hydroxide, or conducting the reaction in the first instance in an aqueous alkali metal hydroxide reaction medium whence the amine catalyst is not required. There is produced in step (1) an Ar' epoxypropyl ether which is caused to react in step (2) with 2-($R^1,R^2,R^3$-3-indolyl)-1,1-dimethylethylamine to yield a product of Formula II depending upon the nature of the Ar'OH starting material employed. Each of reaction steps (1) and (2) takes place facilely in ordinary laboratory or plant equipment under convenient operating conditions.

Heating of epichlorohydrin in substantial molecular excess amount with a phenol Ar'OH containing a drop or two of piperidine as catalyst on a steam bath overnight results in the condensation shown in step (1). Some of the corresponding halohydrin intermediate is also produced and is converted without isolation to the oxirane shown by treatment of the mixture with aqueous alkali metal hydroxide. Alternatively, the Ar'OH phenol and epichlorohydrin can be caused to react in the presence of a sufficient amount of a dilute aqueous alkali metal hydroxide to neutralize the acidic Ar'OH group at room temperature with formation of the desired intermediate

Step (2) is carried out simply by heating the oxirane intermediate produced in step (1) with 2-($R^1,R^2,R^3$-3-indolyl)-1,1-dimethylethylamine either neat or in the presence of a reaction inert organic solvent. No catalyst or condensation agent is required. Suitable solvents include 95% ethanol but other reaction inert organic liquids in which the reactants are soluble may be employed. These include but are not limited to benzene, toluene, tetrahydrofuran, dibutyl ether, butanol, hexanol, methanol, dimethoxyethane, ethylene glycol, etc. Suitable reaction temperatures are from about 60°–200° C.

An alternate variation of the process for the preparation of compounds of Formula II involves reaction of the Ar'OH starting material as defined above with a reactant of the formula

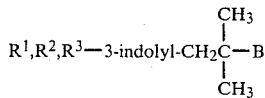

according to reaction (3) of the scheme to yield an intermediate which is transformed to the final product by hydrolysis of hydrogenolysis. The substituent B in the reactant used in step (3) is a group such as shown by III or IV which is reactive with the phenolic hydroxyl group Ar'OH to incorporate into the product an incipient propanolamine side chain.

The reactants for step (3) wherein B has Formula III are prepared by forming the N-benzyl derivative of 2-($R^1,R^2,R^3$-3-indolyl)-1,1-dimethylethylamine and reacting the latter with epichlorohydrin by adaptation of the method of L. Villa et al., Il. Farmaco. Sci., Ed., 24, (3) 349 (1969).

Those reactants wherein B has Formula IV are prepared by reductive alkylation of 2-($R^1,R^2,R^3$-3-indolyl)-1,1-dimethylamine with glyceraldehyde according to known methods, for instance, employing 5% palladium-on-carbon catalyst in an atmosphere of hydrogen with methanol or other suitable non-reactive liquid as solvent. When using an optically active form of glyceraldehyde, an optically active end product of Formula II is obtained. The amino propanediol resulting from the foregoing reductive alkylation reaction is then converted to the desired 2-($R^1,R^2,R^3$-3-indolyl)-1,1-dimethylethyloxazolidinone reactant wherein B has Formula IV by reaction with formaldehyde employing 37% aqueous formaldehyde in refluxing benzene with continued removal of the water by distillation. Esterification with an alkanesulfonyl chloride of the formula $RSO_2Cl$ in which R is a lower alkyl group of 1 to 4 carbon atoms introduces the necessary group which is reactive with Ar'OH.

The intermediate produced by step (3) wherein the B has Formula III is converted in step (4) to a product of Formula II by debenzylation by known means such as catalytic hydrogenation or reaction with sodium in liquid ammonia. The intermediates produced in step (3) wherein B has formula IV are converted to the products of Formula II in step (4) by mild acid hydrolysis. In this instance, care must be taken to avoid decomposition of the reactant since the $R^1,R^2,R^3$-3-indolyl substituent and some of the aryl-substituent Het groups are acid sensitive as is known to those skilled in the art. Aqueous mineral acids of from 0.1 N to 1 N concentration at temperatures of from 20°–100° C. are suitable. The product is recovered as the free base from the hydrolysis mixture by neutralization thereof and collecting the precipitate.

DESCRIPTION OF SPECIFIC EMBODIMENTS 2-(3-Indolyl)-1,1-dimethylethylamine (Chemical Abstracts nomenclature: α,α-dimethyl-1H-indol-3-yl-ethanamine) is prepared by the method of H. R. Snyder, et al., J. Am. Chem. Soc., 69, 3140 (1947) from 3-indolylmethyldimethylamine (gramine) and 2-nitropropane followed by reduction of the resulting 2-(3-indolyl)-1,1-dimethylnitroethane. Various substituted 2-($R^1,R^2,R^3$-3-indolyl)-1,1-dimethylethylamines for application to the synthesis of other compounds of Formula II may be prepared by the method of Arvid Ek, et al., J. Amer. Chem. Soc., 76 5583 (1954).

In the following procedure temperatures are expressed in degrees centigrade (°). Melting points are corrected values according to the U.S.P. method where indicated (corr.). The nuclear magnetic resonance (NMR) spectral characteristics refer to chemical shift (δ) expressed as parts per million (ppm) versus tetramethylsilane (TMS) as reference standard. The relative area reported for the various shifts corresponds to the number of hydrogen atoms of the particular functional type in the molecule, and the nature of the shift as to multiplicity is reported as broad singlet (bs), singlet (s), multiplet (m), doublet (d), triplet (t), or quadruplet (q) with coupling constants (J) reported where appropriate. The format is NMR (solvent): δ(relative area, multiplicity, J value). Abbreviations employed are MeOH (methanol), DMSO (dimethylsulfoxide), DMSO-$d_6$ (deuterodimethylsulfoxide), i-PrOH (isopropanol), abs-.EtOH (absolute ethanol), EtOAc (ethyl acetate), EtOH (95% ethanol), Et$_2$O (diethyl ether), THF (tetrahydrofuran), MEK (2-butanone), i-PrOAc (isopropyl acetate), i-Pr$_2$O (di-isopropyl ether), AcOH (acetic acid), TLC (thin layer chromatography), d (decomposition). Other abbreviations have conventional established meanings. The infrared (IR) spectral descriptions include only absorption wave numbers (cm$^{-1}$) having functional group identification value. KBr was employed as diluent for all IR spectral determinations. TMS was used as internal reference for the NMR spectral determination. The elemental analyses are reported as percent by weight.

Procedure 1. 4-(METHYLSULFONYL)-m-TOLYLOXYMETHYL OXIRANE. To a mixture of 3-methyl-4-methylsulfonylphenol, 8.1 g. (0.0435 mole), and 20.0 g. (0.216 mole) of epichlorohydrin, there are added two drops of piperidine to serve as condensation catalyst and the mixture is heated at 105°–108° for 18 hrs. The excess epichlorhydrin is then removed by distillation using toluene as a chaser. A solution of 2.1 g. of sodium hydroxide in 50 ml. of water and 70 ml. of dimethoxyethane is then added and the mixture is stirred for 2 hrs. with occasional warming on the steam bath to convert any phenoxychlorohydrin compound to the oxirane. The solvent is then removed by distillation in vacuo and the residue is dissolved in a 1:1 (V/V) mixture of ether and benzene. The solution is dried over anhydrous sodium carbonate and examined by thin layer chromatography for purity of the desired oxirane using a 9:1 mixture of chloroform and a methanol for development (R$_f$=0.8). The solvent is then removed by distillation to yield 10.7 g. of a residue constituting the desired oxirane. Measurement of the infrared absorption spectrum is employed to confirm the substantial absence of hydroxyl containing contaminants. This material is suitable for further reaction in Procedure 3 without further purification.

Procedure 2. 2-CHLOROPHENOXYMETHYL OXIRANE. A solution of 12.9 g. of 2-chlorophenol (0.1 mole) in 125 ml. of water containing 6.5 g. (0.162 mole) of sodium hydroxide, and 18.5 g. (0.2 mole) of epichlorohydrin are stirred together at 25° for 20 hrs. The mixture is then extracted twice with 70 ml. portions of methylene chloride. The extract is dried over anhydrous sodium carbonate and the solvent removed by distillation in vacuo. The residue constitutes the desired oxirane and in suitable for further transformation as is described in Procedure 4.

Procedure 3. 1-[[2-(3-INDOLYL)-1,1-DIMETHYLETHYL]AMINO]-3-[4-(METHYLSULFONYL)-m-TOLYLOXY]-2-PROPANOL HYDROCHLORIDE. The oxirane of Procedure 1, 10.7 g., was dissolved in 150 ml. of toluene, 8.2 g. (0.044 mole) of 2-(3-indolyl)-1,1-dimethylethylamine was added and the mixture was refluxed for 18 hrs. The toluene was removed by distillation in vacuo and a portion of the residue was converted to the acetate salt, m.p. 142°–147° C. The structure was confirmed by examination of the infrared absorption and nuclear magnetic resonance spectra. The remainder of the sample was converted to the hydrochloride salt by treatment of an acetonitrile solution thereof with 8 N ethanolic HCl. After recrystallization from CH$_3$CN/MeOH 12.5 g. of product was obtained, m.p. 174.0°–177.0° (corr.).

Anal. Found: C, 59.40; H, 6.90; N, 5.87.

NMR (DMSO-d$_6$): 1.29 (6, s); 2.52 (3, s); 3.12 (3, s); 3.16 (4, m); 4.18 (3, m); 5.95 (1, bs); 7.10 (8, m); 9.00 (2, bs); and 11.12 (1, bs).

IR: 740, 765, 1120, 1290, 1450, 1590, and 3270.

Procedure 4. 1-(2-CHLOROPHENOXY)-3-[[2-(3-INDOLYL)-1,1-DIMETHYLETHYL]AMINO]-2-PROPANOL. A portion of the oxirane produced in Procedure 2, 7 g. (0.033 mole), was refluxed in solution with 6.3 g. (0.033 mole) of 2-(3-indolyl)-1,1-dimethylethylamine in 70 ml. of ethanol. After 24 hrs. the solvent was removed by distillation in vacuo and the viscous liquid residue was dissolved in 200 ml. of ether, acidified with 8 N ethanolic HCl and the solvents again removed by distillation. Crystallization was induced by adding acetonitrile and rubbing with a glass rod; recrystallized from acetonitrile and di-isopropyl ether to yield 4.8 g. of product, m.p. 150.5°–153.5° C. (corr.).

Anal. Found: C, 61.54; H, 6.41; N, 6.94.

NMR (DMSO-d$_6$): 1.28 (6, s); 3.22 (4, m); 4.25 (3, m); 5.96 (1, bs); 7.23 (9, m); 8.84 (2, bs); and 11.12 (1, bs).

IR: 745, 1250, 1455, 1480, 1590, and 2780.

By adaptation of the foregoing procedures, the products listed in the following table were prepared.

PRODUCTS OF FORMULA II
PROCEDURES 5-8

| Procedure No. | Ar-Het | m.p.° (corr.) | Recryst. Solvent | Elemental Analysis | NMR(DMSO-d$_6$) | IR |
|---|---|---|---|---|---|---|
| 5 | 2-(1H-pyrrol-1-yl)-phenyl | 124.0–126.0 base | EtOAc/i-PrOAc | C, 74,40<br>H, 7.32<br>N, 10.38 | 1.10 (6,s)<br>2.33 (1,bs)<br>2.80 (4,m)<br>3.96 (3,m)<br>5.92 (1,bs)<br>6.33 (2,m)<br>7.19 (11,m)<br>8.10 (1,bs) | 740, 110, 1230,<br>1450, 1510, 1590,<br>3160, 3400 |
| 6 | (structure with N, C=O, CONH$_2$, methylphenyl) | 224.5–227.5 hydrochloride hemihydrate | abs.EtOH/EtOAc | C, 61.41<br>C, 61.24<br>H, 6.90<br>H, 6.59<br>N, 10.81<br>N, 10.72<br>Cl, 7.34 | 1.30 (6,s)<br>2.55 (2,m)<br>3.25–4.25 (10,m)<br>6.05 (1,bs)<br>7.35 (11,m)<br>8.90 (1,bs)<br>9.31 (1,bs) | 760, 1430, 1510<br>1600, 1680, 3400 |

-continued

PRODUCTS OF FORMULA II
PROCEDURES 5-8

| Procedure No. | Ar-Het | m.p.° (corr.) | Recryst. Solvent | Elemental Analysis | NMR(DMSO-$d_6$) | IR |
|---|---|---|---|---|---|---|
| 7 | (structure with CH$_3$O, C$_2$H$_5$, N=N ring) | 181–182 | dioxane/ EtOAc | C, 69.67 H, 7.30 N, 12.39 | 1.09 (6,s) 1.35 (3,t, 7.1 Hz) 2.85 (4,m) 3.26 (2,q, 7.1 Hz) 4.03 (3,s) 4.28 (3,m) 7.33 (7,m) 9.19 (1,s) | 750, 1240, 1450, 1480, 1510, 1625, 2980, 3430 |
| 8 | (structure with CH$_3$O, C$_2$H$_5$, N=N ring) | 134–136 | butanone | C, 69.55 H, 7.25 N, 12.17 | 1.05 (6,s) 1.36 (3,t, 7.2 Hz) 2.87 (4,m) 3.22 (2,q, 7.2 Hz) 4.00 (3,s) 4.20 (3,m) 5.02 (1,bs) 5.18 (1,bs) 7.32 (7,m) 9.16 (1,s) 11.20 (1,bs) | 750, 1240, 1430 1470, 1500, 1620 2970, 3420 |

Procedure 9A. 1-[[2-(1-METHYL-3-INDOLYL)-1,1-DIMETHYLETHYL]AMINO]-3-(2-METHYL-PHENOXY)-2-PROPANOL HYDROCHLORIDE. (2-Methylphenoxymethyl)oxirane 4.37 g. (0.027 mole) and α,α-1-trimethyl-1H-dinol-3-yl-ethanamine 5.11 g. (0.025 mole) are mixed and heated at 140° for 30 min. to give the desired product; m.p. 189.5°–192.5° (corr.), after recrystallization from abs. EtOH.

Anal. Found: C, 68.40; H, 7.50; N, 6.86.

NMR (DMSO-$d_6$): 1.32 (6,s); 2.22 (3,s); 3.28 (4,m); 3.79 (3,s); 4.30 (3,m); 5.65 (1,bs); 7.22 (9,m); 9.30 (2,bs).

IR: 745, 1120, 1250, 1380, 1475, 1500, 1590, 1600, 2800, and 2950.

The intermediate amine is prepared as follows.

Procedure 9B. α,α-1-TRIMETHYL-1H-INDOL-3-YL-ETHANAMINE. Seven grams (0.106 mole) of 85% KOH was ground in a mortar and quickly transferred to a N$_2$-flushed 25 ml. Erlenmeyer flask. DMSO (55 ml.) was added and the mixture was stirred 5 min. Additions of 2-(3-indolyl)-1,1-dimethylethylamine (5 g., 0.27 mole) and iodomethane (3.78 g., 0.027 mole) were each followed by 45 min. stirring, after which the suspension was quenched in 300 ml. of water. Extraction of the mixture with EtOAc, followed by washing of the extracts with water and brine afforded a clear solution which was dried over anh. MgSO$_4$ and evaporated in vacuo (20 mm) to give 5 g., of yellow oil. The hydrochloride salt crystallized from i-PrOH-EtOAc, m.p. 138°–148° (prior shrinking). The free base was used in Procedure 69A without further purification.

Procedure 10A. 2-[2-HYDROXY-3-[[2-(2-METHYL-1H-INDOL-3-YL)-1,1-DIMETHYLETHYL]AMINO]PROPOXY]BENZONITRILE OXALATE (2:1). The method of Procedure 4 was applied to the reaction of 10.1 g (0.05 mole) of 2-(2-methyl-3-indolyl)-1,1-dimethylethyl amine and 12.3 g (0.07 mole) of 2-[2,3-epoxy)propoxy]benzonitrile for the production of the desired product. It was purified by column chromatography on silica gel employing 9:1 CHCl$_3$:MeOH for elution as the free base. The free base was an oil which was dissolved in warm isopropanol and acidified with oxalic acid resulting in precipitation of the oxalate (2:1) salt m.p., 218°–221°.

Anal. Found: C, 68.12, H, 6.74; N, 9.76.

NMR (DMSO-$d_6$): 1.18 (6,s); 2.35 (3,s); 3.01 (4,m); 4.20 (3,m); 7.22 (8,m); 7.55 (3,bs); 10.85 (1,bs).

IR: 750, 1290, 1450, 1460, 1490, 1580, and 1600.

Procedure 10B. 2-METHYLGRAMINE. AcOH, 236 ml., was mixed with cooling and stirring with 62 ml. of 37% formaldehyde at 10°, and 154 ml of 25% aqueous dimethylamine was added dropwise with cooling so as to maintain the temperature at 10°. A solution of 100 g of 2-methylindole in 160 ml of dioxane was then added dropwise with cooling, again maintaining the temperature at 10°. The mixture was stirred at ice temperature for 1 hour and then overnight at room temperature. The mixture was then poured into 2.0 of water with stirring. A small amount of insoluble material was removed by filtration. The filtrate was treated with activated charcoal, filtered again, and the filtrate cooled and basified by the dropwise addition of about 225 ml. of 50% aqueous sodium hydroxide. The product was collected by filtration, washed with water, and air dried, yield 96 g. This material was dissolved in 700 ml of dilute aqueous HCl, treated with activated carbon, filtered, and again basified after diluting to 2 l. with water. The product was collected, air dried, and recrystallized from acetonitrile, yield 72 g., m.p. 117°–119°.

Procedure 10C. 2-METHYL-3-(2-METHYL-2-NITROPROPYL)INDOLE. A mixture of 15.0 g (0.069 mole) of 2-methylgramine, 44.0 g. (0.49 mole) of 2-nitropropane, and 2.9 g (0.072 mole) of sodium hydroxide pellets is prepared and heated at reflux for 18 hours. This is allowed to cool to room temperature, and 60 ml of 10% aqueous acetic acid is added. Stirring at room temperature is continued for 1 hr. and the mixture is then diluted with about 150 ml of ether. The ether layer is removed and washed with 3 portions of water. The ether solution is then dried over magnesium sulfate, and the solvent removed by distillation yielding 16.5 g of dark oil which crystallized on standing; recrystallized from EtOH-H$_2$O, yield 12.6 g., m.p. 101°–103°.

Procedure 10D. α,α-2-TRIMETHYL-1H-INDOL-3-YL-ETHANAMINE. The nitro compound produced in Procedure 10C, 0.6 g (0.054 mole) was dissolved in 150 ml of 95% aqueous ethanol, 8.0 g of activated Raney nickel catalyst was added. The mixture was then heated to boiling and a solution of 13.1 g of 85% hydrazine hydrate in 13 ml of ethanol was added dropwise. The mixture was refluxed for 2 hrs., and the treatment with Raney nickel and hydrazine hydrate was repeated with fresh portions thereof. The mixture was refluxed for 1 hr., and then filtered. The solvent was removed from filtrate by distillation, and the residual oil became crystalline on standing. This was dissolved in aqueous HCl and washed with 3 portions of methylene chloride. The aqueous layer was then treated with activated charcoal, filtered, and basified with 4 N sodium hydroxide. The product which separated was recovered by extraction with 3 portions of methylene chloride, evaporation of the solvent, and crystallization from isopropyl ether, yield 5.7 g., m.p. 99°–107°.

Procedure 11A. 2-[2-HYDROXY-3-[[2-(5-METHOXY-1H-INDOL-3-YL)-1,1-DIMETHYLETHYL]AMINO]PROPOXY]BENZONITRILE HYDROCHLORIDE. A mixture of 4.4 g. (0.025 mole) of 2-[(2,3-epoxy)propoxy]benzonitrile and 5.4 g. of (0.025 mole) of α,α-dimethyl-5-methoxy-1H-indol-3-yl-ethaneamine was melted with stirring at 120°–130° for 1 hr. The mixture was then cooled, triturated with 250 ml. of EtOAc, and acidified with 5 N ethanolic HCl to pH 2. Unreacted starting material weighing 3 g. was removed as a brown, tacky solid by filtration. On standing overnight, the desired product separated from the filtrate as a white crystalline solid which was collected in 3 crops, all exhibiting $R_f$ 0.3 by TLC on silica gel employing 9:1 CHCl$_3$:MeOH containing ammonia. This material was recrystallized from MEK:EtOH(20:1), yield 6.1 g, m.p. 164°–166°.

Anal. Found: C, 64.14; H, 6.54; N, 9.68.

NMR (DMSO-d$_6$): 1.33 (6,s); 3.18 (4,m); 3.79 (3,s); 4.31 (3,m); 6.06 (1,d, 4.8 Hz); 7.20 (8,m); 8.85 (1,bs); 9.35 (1,bs); 11.00 (1,bs).

IR: 760, 1260, 1290, 1450, 4190, 1580, 1600, 1620, 2220, and 3400.

Procedure 11B. 5-METHOXYGRAMINE. This material was prepared from 5-methoxyindole, formaldehyde, and dimethylamine by reaction thereof in dioxane/aqueous acetic acid according to the method of Procedure 10B. From 58.7 g. of 5-methoxyindole, 40 g. of crude 5-methoxygramine was obtained which was recrystallized from 200 ml. of i-Pr$_2$O, yield, 29.7 g., m.p. 118°–122°. Identity was confirmed by inspection of its NMR spectrum.

Procedure 11C. 5-METHOXY-3-(2-METHYL-2-NITROPROPYL)INDOLE. This material was prepared by the reaction of 5-methoxygramine (Procedure 11B) and 2-nitropropane substantially described in Procedure 10C. The product was initially recovered as a dark oil which crystallized from i-Pr$_2$O solution after treatment thereof with activated carbon, yield 31.3 g. (from 33 g. of 5-methoxygramine), m.p. 83°–85°. The identity of the product was confirmed by inspection of its NMR spectrum.

Procedure 11D. 5-METHOXY-α,α-DIMETHYL-1H-INDOL-3-YL-ETHANEAMINE. The nitro compound produced in Procedure 11C was reduced with Raney nickel and hydrazine hydrate according to the method of Procedure 10D. The structure of the product was confirmed by examination of the NMR spectrum, m.p. 114°–116°, yield 25.8 g. from 31.3 g. of nitro compound.

Procedure 12A. 1-[[2-(5-BROMO-3-INDOLYL)-1,1-DIMETHYLETHYL]AMINO]-3-(2-METHYL-PHENOXY)-2-PROPANOL HYDROCHLORIDE. (2-Methylphenoxymethyl)oxirane, 4.1 g. (0.025 mole) and 6.65 g. (0.025 mole) of 5-bromo-α,α-dimethyl-1H-indol-3-yl-ethaneamine were mixed and heated at 140° for 1 hr. The mixture was then cooled and dissolved in 40 ml. of acetonitrile while still warm. The product was converted to the hydrochloride salt by treatment of the solution with 5 N ethanolic HCl. The solvent was removed by distillation and the residue dissolved in 30 ml. of acetonitrile. The product crystallized from this solution, yield 11.0 g., m.p. 197°–199°. This material was recrystallized from methanol/isopropanol, yield 8.0 g., m.p. 198.0°–200.0° dec. (corr.).

Anal. Found: C, 56.10; H, 6.25; N, 5.79.

NMR (DMSO-d$_6$): 1.30 (6,s); 2.20 (3, s); 3.19 (4,m); 4.07 (2,m); 4.36 (1,m); 5.30 (1,bs); 7.11 (7,m); 7.86 (1,m); 8.80 (1,bs).

IR: 760, 1250, 1470, 1500, 1610, 2800, 2980, and 3400.

Procedure 12B. 5-BROMOGRAMINE. This material was prepared by the method of Procedure 10B from 49.5 g. of 5-bromoindole, 20 ml. of 37% aqueous formaldehyde, 55 ml. of 25% aqueous dimethylamine, 250 ml. of acetic acid and 250 ml. of dioxane; yield 60.6 g., m.p. 154°–156° C. The structure was confirmed by examination of the NMR spectrum.

Procedure 12C. 5-BROMO-3-(2-METHYL-2-NITROPROPYL)INDOLE. 5-Bromogramine, 60.0 g., 165 g. of 2-nitropropane, and 10.5 g. of sodium hydroxide pellets were caused to react under the conditions of Procedure 10C. The product was recovered as a dark syrup-like liquid from which the crystalline product was obtained by dissolving in i-Pr$_2$O. The crystalline material was recrystallized from i-Pr$_2$O to yield 48.6 g. of tan crystalline product, m.p. 106°–109°. The structure was confirmed by examination of the NMR spectrum.

Procedure 12D. 5-BROMO-α,α-DIMETHYL-1H-INDOL-3-YL-ETHANEAMINE. 5-Bromo-3-(2-methyl-2-nitropropyl)indole, 5.9 g. ws reduced with Raney nickel and hydrazine hydrate according to the method of Procedure 10D. The crude product was purified by dissolving in 200 ml. of dilute hydrochloric acid, treating with activated charcoal, filtering, and basifying the filtrate with 10% aqueous sodium hydroxide. Yield 3.8 g. of white powder, m.p. 150°–155° C.

Procedure 13. TABLETS. The following ingredients ae blended in the proportions by weight indicated according to conventional pharmaceutical techniques to provide a tablet base.

| Ingredient | Amount |
| --- | --- |
| Lactose | 79 |
| Corn starch | 10 |
| Talcum | 6 |
| Tragacanth | 4 |
| Magnesium stearate | 1 |

This tablet base is blended with sufficient 1-[2-[2-hydroxy-3-[[2-(1H-indol-3-yl)-1,1-dimethylethyl]amino]propoxy]phenyl]-5-oxopyrrolidone-3-carboxamide hydrochloride hemihydrate (Procedure 6) to provide tablets containing 10, 20, 40, 80, 160 and 320 mg. of active ingredient, and compressed in a conventional tablet press.

Procedure 14. DRY FILLED CAPSULES. The following ingredients are blended in a conventional manner in the proportion by weight indicated.

| Ingredient | Amount |
| --- | --- |
| Lactose, U.S.P. | 50 |
| Starch | 5 |
| Magnesium stearate | 2 |

Sufficient 1-[2-[2-hydroxy-3-[[2-(1H-indol-3-yl)-1,1-dimethylethyl]amino]propoxy]phenyl]-5-oxopyrrolidone-3-carboxamide hydrochloride hemihydrate (Procedure 6) is added to the blend to provide capsules containing 10, 20, 40, 80, 160 and 320 mg. of active ingredient which is filled into hard gelatin capsules of a suitable size.

Procedure 15. SOLUTION. A solution of 1-[(4-ethyl-7-methoxyquinazolin-6-yl)oxy]-3-[[2-(3-indolyl)-1,1-dimethylethyl]amino]-2-propanol (Procedure 7) is prepared from the following ingredients.

| Ingredient | Amount |
| --- | --- |
| Active ingredient | 20 g. |
| Sucrose, U.S.P. | 400 g. |
| Sorbitol, U.S.P. | 100 g. |
| Bentonite | 20 g. |
| Flavors, q.s. | |
| Water, q.s. | 1 l. |
| 0.5N HCl, q.s. | pH 3.0 |

Each milliliter of the solution contains approximately 20 mg. of the active ingredient.

By application of the methods of Procedures 1 or 2 to the appropriate phenol, or by other conventional methods, the oxiranes referred to below with respect to Procedures 16–18, and 22–30, are prepared and then converted to products of Formula II by reaction with 2-(3-indolyl)-1,1-dimethylethylamine according to Procedures 3 or 4, with α,α-1-trimethyl-1H-indol-3-ylethanamine according to Procedure 9A, with 2-(2-methyl-3-indolyl)-1,1-dimethylethyl amine according to Procedure 10A, with α,α-dimethyl-5-methoxy-1H-indol-3-ylethanamine according to Procedure 11A, or with 5-bromo-α,α-dimethyl-1H-indol-3-ylethanamine according to Procedure 12A. With respect to Procedures 19, 20, and 21, the phenolic compounds shown are converted to products of Formula II by reactions 3 and 4 shown in the above reaction scheme.

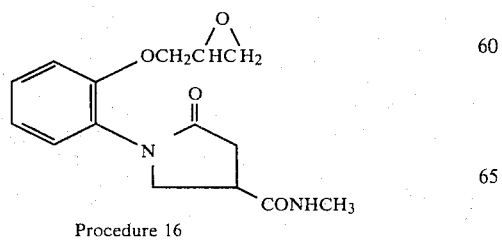

Procedure 16

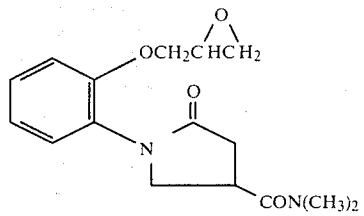

Procedure 17

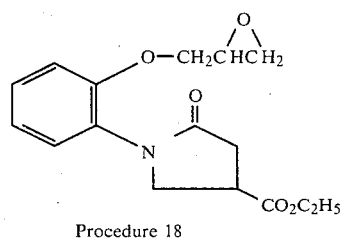

Procedure 18

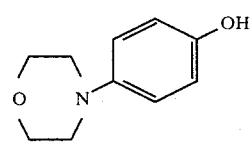

Procedure 19

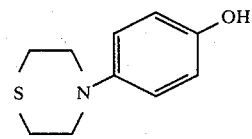

Procedure 20

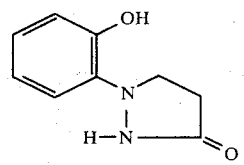

Procedure 21

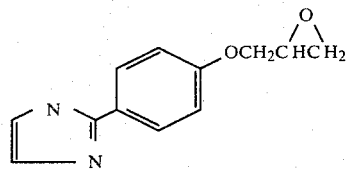

Procedure 22

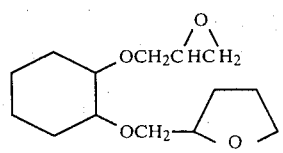

Procedure 23

-continued

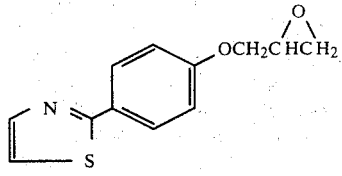
Procedure 24

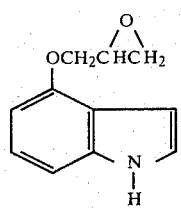
Procedure 25

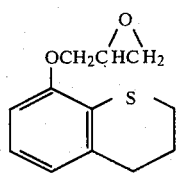
Procedure 26

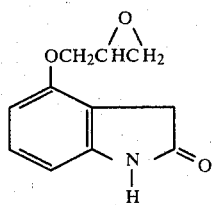
Procedure 27

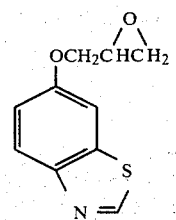
Procedure 28

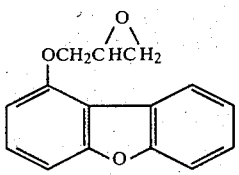
Procedure 29

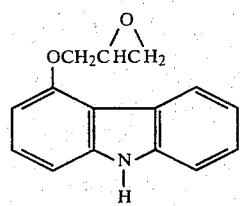
Procedure 30

BIOLOGICAL EVALUATION

Three biological tests have been used to gauge the effectiveness of a number of the compounds of Formula II as β-adrenergic blocking vasodilators. They are described in Procedures 31, 32, and 33 and the results shown in the table where the test compounds are identified by the Procedure No. for their preparation. Where a dash (—) appears in the table, the test was not completed.

Procedure 31. Beta-blocking potency was estimated in the conscious rat (Test 349F) and is reported as a potency, compared to propranolol, with respect to prevention of the isoproterenol-induced increase in heart rate at 2 and 4 hrs. after oral dosing. The doses of propranolol and test compound necessary to evoke the same blocking effect are determined and the former is divided by the latter to give a relative potency factor.

Procedure 32. The efficacy of antihypertensive agents other than adrenergic β-receptor blocking agents, is commonly estimated in the spontaneous hypertensive rat (Test 410C). Values for blood pressure listed in the table represent changes (positive or negative) in the blood pressure of test animals prior to and 22 hrs. after oral doses of 100 mg/kg of test compounds; the observed percentage change in heart rate is noted as well. A fall in blood pressure in the range of 19–24 mmHg is considered "questionable." "Active" and "inactive" designations are decreases greater and less than that range.

Procedure 33. The angiotensin-maintained ganglion-blocked rat model is utilized as a screening test for estimation of the vasodilator component of activity. Values listed in the table note percentage changes in blood pressure in anesthetized rats 30 min. after intravenous dosing with test compound at 3 mg/kg. Borderline activity is defined as a 15–20% decrease in blood pressure measured 30 min. after dosing. "Active" and "inactive" designations are decreases greater and less than that range.

| | Adrenergic β-Receptor Blocking and Vasodilator Action | | | | |
|---|---|---|---|---|---|
| Proc. No. | β-Adrenergic Block[1] | Antihypertensive | | Other | ALD$_{50}$[4] |
| | | Δmm Hg[2] | %Δ H.R.[3] | | |
| 5 | 5 | −11.4 | −18 | 7,9 | 250 |
| 6 | 0.5 | −20 | 0 | 8,9 | — |
| 7 | 6 | −27.2 | −10 | 10 | — |
| 8 | 5 | −4.5 | −4.5 | 11 | >2000 |

[1]Potency factor relative to propranolol - Procedure 31.
[2]Change in blood pressure - Procedure 32 dose 100 mg/kg p.o.
[3]Percent change in heart rate - Procedure 32, dose 100 mg/kg P.O.
[4]Mouse treated orally. Approximate value.
[5]Adrenergic β-receptor blocking action was demonstrated in vitro using tracheal and atrial tissue.
[6]Adrenergic β-receptor blocking action could not be demonstrated in vitro.
[7]Questionable activity against ouabain-induced ventricular tachycardia in the dog.
[8]5% decrease in b.p. in Procedure 33.
[9]β-Adrenergic block and hypotensive action observed in the anesthetized dog.
[10]Active against oubain-induced ventricular tachycardia in the dog.
[11]Anti-arrhythmic action: active for reduction of ectopic heart beats in surgically induced arrhythmia in the dog, Harris, Circulation, 1, 1318 (1950).

Procedure 34. N-(2-HYDROXYPHENYL)-2-OXOPYRROLIDINE-4-CARBOXAMIDE. A mixture of 21.8 g. (0.2 mole) of o-aminophenol and 31.6 g. (0.2 mole) of dimethyl itaconate in a 500 ml. round bottomed flask was heated to 190° for 1 hr. and volatile by-products were allowed to escape. The residue was taken up in 150 ml. of boiling EtOAc and diluted with 300 ml. of (i-Pr)$_2$O. After the solution had cooled, it was clarified by filtration, evaporated to a volume of 100 ml., and chilled at 5°. The tan crystalline solid was collected on a filter, and dried in air to give 22 g. of crude hydroxy ester, m.p. 120°–124°. Conversion of 5.0 g. (0.0212 mole) of the foregoing hydroxy ester was accomplished by stirring with 50 ml. of concentrated NH$_4$OH at 25° for 24 hrs. Volatile material was removed by distillation at 95°/50 mm and the red glassy residue was taken up in a small amount of EtOAc-MeOH and allowed to stand. Crystals were deposited on standing. They were collected, and recrystallized from i-PrOH-EtOAc to give 3.12 g. of the desired product, m.p. 133°–135°, which was further purified by recrystallization from CH$_3$CN using activated carbon, yield 1.9 g., m.p. 135°–138°. This material was used without further purification as starting material for Procedure 6.

Procedure 35. 4-ETHYL-6-METHOXYQUINAZOLIN-7-OL. A solution of 4-ethyl-6,7-dimethoxyqunazoline (100 g., 0.46 mole, m.p. 146°–148°) in 280 ml. of 48% hydrobromic acid was refluxed 3.5 hrs. at which time only a trace of this starting material was evident by TLC (9:1 CHCl3—MeOH; silica). The mixture was cooled to 25° and neutralized (pH 7) with concentrated NH4OH. After the suspension had been chilled overnight (5°), the crude grey-green precipitate was collected on a filter and dried—first overnight in air and then in a vacuum oven at 50°/60 mm for 18 hrs. The dry solid (70 g., m.p. 210°–215°) was recrystallized from MeOH-(i-Pr)2O to give 42 g. (43%) of chartreuse powder, m.p. 221°–224° (uncorr.). The identity of the product was confirmed by examination of the IR spectrum. This material was used as starting material for Procedure 8.

Procedure 36. 4-ETHYL-7-METHOXYQUINAZOLIN-6-OL. 2-Methoxyphenol was esterified by reaction with chloroacetyl chloride to give in 75% yield, 2-methoxyphenyl chloroacetate, m.p. 60°–61.5°. This material was acylated with propionic acid in the presence of polyphosphoric acid to produce 2-methoxy-5-propionylphenyl chloroacetate in 75% yield, m.p. 77°–79.5° C. This ester was hydrolyzed with sodium acetate in methanol to yield 1-(3-hydroxy-4-methoxyphenyl)-1-propanone, m.p. 91°–92°, yield 90%. Benzylation of the latter by treatment in acetone with benzyl chloride and potassium carbonate yielded 1-(3-benzyloxy-4-methoxyphenyl)-1-propanone, m.p. 83°–85°, yield 96%. The latter was then nitrated by treatment with 1:3 nitric acid/acetic acid at 18°–20° to yield 1-(2-nitro-4-methoxy-5-benzyloxyphenyl)-1-propanone, m.p. 120.5°–123°, yield 65%. Reduction of this material with hydrazine hydrate and Raney nickel yielded 1-(2-amino-4-methoxy-5-benzyloxyphenyl)-1-propanone. The latter was cyclized by treatment with formic acid and formamide to yield 6-benzyloxy-4-ethyl-7-methoxyquinoline, yield 80%, m.p. 132°–134°. Catalytic hydrogenation of the latter resulted in debenzylation to yield 4-ethyl-7-methoxyquinolin-6-ol in 85% yield, m.p. 200°–202° which was required as starting material for Procedure 7.

Procedure 37. 7-(2,3-EPOXYPROPOXY)-4-ETHYL-6-METHOXYQUINAZOLINE. A suspension of finely powdered anhyd. K2CO3 in 70 ml. of DMSO containing 6.2 g. (0.03 mole) of 4-ethyl-6-methoxyquinazolin-7-ol was stirred at 25° for 15 min. Epibromohydrin (10.3 g., 0.075 mole) was added in one portion and stirring was continued for 24 hrs. at 25°, after which the mixture was poured into 800 ml. H2O and extracted twice with 200 ml. EtOAc and twice with 100 ml. CH2Cl2. The combined organic layers were dried (anhyd. Na2CO3), filtered and evaporated at 100°/60 mm to afford 13.5 g. of crude yellow solid which was recrystallized from EtOAc to give 4.75 g. of the pure intermediate, m.p. 120.0°–121.0° (corr.). Elemental analysis for C, H, and N confirmed the formula C14H16N2O3.

Procedure 38. 6-(2,3-EPOXYPROPOXY)-4-ETHYL-7-METHOXY-QUINAZOLINE. 4-Ethyl-7-methoxyquinazolin-6-ol was treated as described in Procedure 37, yield 67%, m.p. 120.0°–122.0° after recrystallization from EtOAc. Elemental analysis for C, H, and N confirmed the formula C14H16N2O3.

What is claimed is:

1. A compound selected from the group consisting of

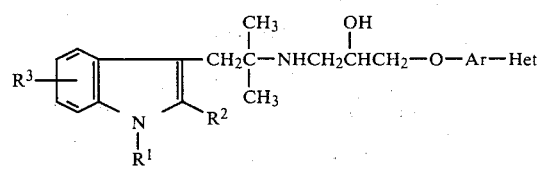

and the acid addition salts thereof wherein
$R^1$ or $R^2$ is hydrogen and the other is hydrogen or alkyl having 1 to 4 carbon atoms,
$R^3$ is H, halogen, alkyl having 1 to 4 carbon atoms, or alkoxy having 1 to 4 carbon atoms and is located in the 4-, 5-, 6-, or 7-positions of the indole ring,
Ar is phenylene,
Het is an Ar-attached heterocyclic substituent selected from the group consisting of
1-pyrrolyl,
2-oxo-1-pyrrolidinyl having a substituent in the 4-position selected from aminocarbonyl, alkylaminocarbonyl, dialkylaminocarbonyl, and alkoxycarbonyl, wherein said alkyl and alkoxy groups have 1 to 4 carbon atoms, and
furfuryloxy.

2. The compound of claim 1 wherein $R^1$, $R^2$, and $R^3$ are hydrogen and Het is 1-pyrrolyl.

3. The compound of claim 2, 1-[[2-(3-indolyl)-1,1-dimethylethyl]amino]-3-[2-(1H-pyrrol-1-yl)phenoxy]-2-propanol.

4. The compound of claim 1, 1-[2-[2-hydroxy-3-[[2-(1H-indol-3-yl)-1,1-dimethylethyl]amino]propoxy]phenyl]-5-oxopyrrolidine-3-carboxamide.

5. The compound of claim 1 wherein Het is the furfuryloxy located in the 2-position.

* * * * *